Oct. 12, 1971 J. W. PATTERSON Plant Pat. 3,074
VARIETY OF ROSE
Filed Aug. 4, 1969
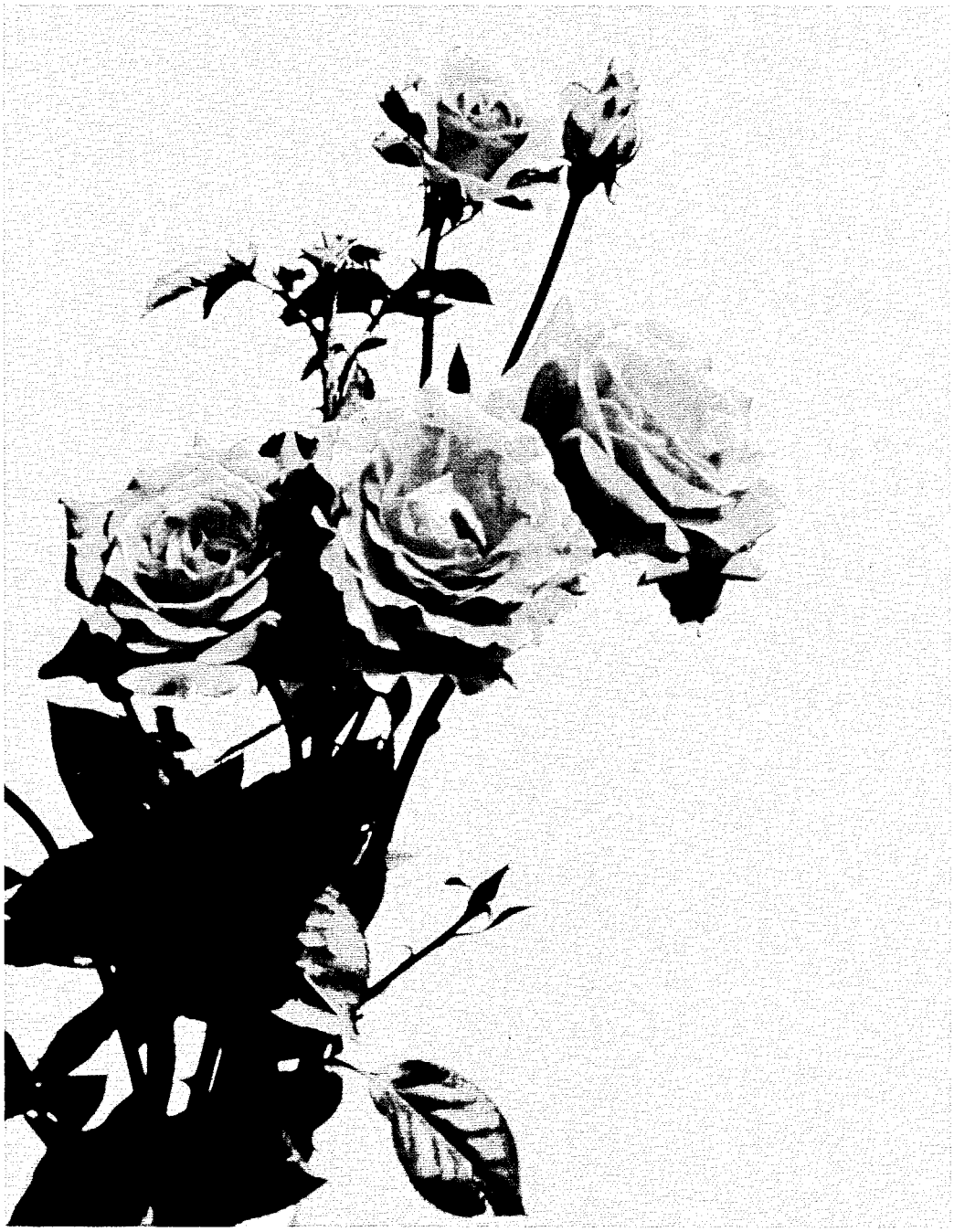

United States Patent Office

Plant Pat. 3,074
Patented Oct. 12, 1971

3,074

VARIETY OF ROSE

John W. Patterson, 6518 Kernel, Houston, Tex. 77071

Filed Aug. 4, 1969, Ser. No. 847,474
Int. Cl. A01h *5/00*
U.S. Cl. Plt.—19 1 Claim

The present invention relates to a new and distinct variety of rose plant of the grandiflora class, which was originated by me by crossing the variety "Queen Elizabeth" (Plant Patent No. 1,259) with the variety "Happiness" (Plant Patent No. 911).

The primary objective of this breeding was to produce a new rose variety of outstanding features such as the continuous flower production and hearty growth of the seed parent, "Queen Elizabeth," but bears flowers similar to the pollen parent "Happiness" in texture and long life of the flowers as cut flowers. The objectives were substantially achieved along with other desirable characteristics, as evidenced by the following description of the new variety which distinguish it from its parents, as well as from all other varieties of which I am aware:

(1) Good growing and flower producing habits;
(2) Medium to large flowers borne singly and in clusters;
(3) Good flower form;
(4) Moderate flower fragrance;
(5) An abundance of dark green, glossy foilage;
(6) Better than average disease resistance, particularly with respect to mildew and blackspot, as compared with other varieties grown under comparable conditions at Houston, Tex.;
(7) A distinctive attractive general color tonality of the flowers corresponding to Cardinal Red, Plate 822/2 in the newly opened flowers, and to near Tyrian Purple, Plate 727/1, page 159, in the three-days open flowers.

In comparison with its seed parent "Queen Elizabeth," the new variety does not grow quite as tall; it is more disease resistant, with respect to mildew and blackspot; flowers are an entirely different color.

As compared with its pollen parent, "Happiness," the flowers are a lighter color, and the new variety is a better, stronger grower and produces many more blooms.

Asexual reproduction of my new variety by budding at Houston, Tex. and also at Tyler, Tex. and Wills Point, Tex., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character. The frosted appearance of the newly opened bloom adjacent the bud was caused by the light reflecting from the velvety petal surfaces rather than a fading thereof as is seen in the fully open blooms. The actual newly opened blossom colors are better represented by the bud colors.

The following is a detailed description of the new variety, with color terminology in accordance with the Horticultural Colour Chart of the Royal Horticultural Society:

Type: Bush; seedling.
Class: Grandiflora
Breeding: Seedling.
*Seed parent.*—"Queen Elizabeth."
*Pollen parent.*—"Happiness."

The cultivar name is "Ruby Dee."

Propagation: Holds its distinguishing characteristics through succeeding propagation by budding.

*Flower*

Locality where grown and observed: Houston, Tex.
Blooming habit: Recurrent—continuous through growing season.
Flowers borne: Singly to stem sometimes, more often in clusters; on medium length stems.
Fragrance: Moderate. Nature—tea.
Bud:
*Peduncle.*—Medium to long length; medium diameter; strong erect. Bark.
*Color.*—Scheeles Green, Plate 860, page 175.
*Thorns.*—None.
*Prickles.*—Many.
*Before calyx breaks.*—Size—medium. Form—long, pointed; with foliaceous appendages on the surface of the bud; with slender foliaceous partextending beyond the tip of the bud equal to ¾ or more of its length. Color—near Scheeles Green, Plate 860/1, page 175, with foliaceous part slightly overlaid with Indian Lake, Plate 826/3, page 170.
*As calyx breaks.*—Color (outside of petal)—Indian Lake, Plate 826, page 170. Sepals—Inner surface with fine wooly tomentum. Outside surface—Color—Scheeles Green, Plate 860, page 175.
*As first petal opens.* — Size — large. Form—Ovid. Color: Outside—base of petal Cardinal Red, Plate 822/3, page 168, upper portion of petal Cardinal Red, Plate 822, page 168; inside—near Currant Red, Plate 821, page 167.
*Opening.*—Opens up well outdoors; no unusual characteristics attributed to weather conditions.
Bloom:
*Size (when fully open).*—Large, about 5 inches.
*Petalage.*—Double; 45 petals; arranged regularly.
*Form.*—Full and high centered at first, opening with petals slightly rolled outward at maturity.
Petals:
*Texture.*—Thick, slightly velvety both inside and outside.
*Shape.*—Outer petals—obovate; intermediate petals—obvoate. Inner petals—obvoate. All with slightly pointed apex, and some with one notch.

This description of a newly opened flower was made from a rose grown outdoors during the month of June at Houston, Tex.

*Color.—Outer petal*—outside surface—near Current Red, Plate 821/7, Page 167; inside surface—base of petal Tyrian Purple, Plate 727, page 159, with remainder near Cardinal Red, Plate 822/1, page 168. *Intermediate petal*: outside surface—Current Red, Plate 821/2, page 167; inside surface—base of petal Currant Red, Plate 321/1, page 167, with remainder of petal Cardinal Red, Plate 822/2, page 168. *Inner petal*: outside surface— upper portion of petal Cardinal Red, Plate 822/2, page 168, lower portion Cardinal Red, Plate 822/3, page 168; inside surface—upper portion of petal Cardinal Red, Plate 822/2, page 168, base of petal Cardinal Red, Plate 822/3, page 168.

This description was made from a rose that was open for three days outdoors during the month of June at Houston, Tex.

*Color.—Outer petal*—outside surface—Currant Red, Plate 821/3, page 167; inside surface—near Tyrian Purple, Plate 727/1, page 159. *Intermediate petal*: outside surface—Tyrian Purple, Plate 727/3, page 159; inside surface—near Magenta Rose, Plate 027, page 113. *Inner petal*: outside surface—near Spirea Red, Plate 025/1, page 112; inside surface—Cardinal Red, Plate 822, page 168.

*General color effect.*—Newly opened flower—Cardinal Red, Plate 822/2, page 168. Three days open—near Tyrian Purple, Plate 727/1, page 159 with outer petals shading to lighter tone near Magenta Rose, Plate 027/1, page 113.

*Behavior of petals.*—Long lasting; drops off cleanly.

*Flower longevity.*—Cut roses grown outdoors and kept at living room temperature from 3 to 4 days in June.

*Reproductive organs*

Stamens: Average amount; arranged regularly about pistils.

Filaments: Some short, some medium and some long length; most with anthers. Color—Magenta Rose, Plate 027/1, page 113.

Anthers: Medium large; open at various times. Color—Yellow Ochre, Plate 07, page 101.

Pollen: Average amount. Color—near Indian Yellow, Plate 6/3, page 6.

Pistils: Many.

Sytles: Uneven and bunched. Medium to long length.

Stigma: Color—near Rose Opal, Plate 022/1, page 110.

Ovularies: Most enclosed in receptacle.

Hips: Moderate amount.

Sepals: Permanent; medium to long length; spear shaped. Color—inside—Scheeles Green, Plate 860/2, page 175, overlaid with white fuzz; outside—Scheeles Green, Plate 860, page 175.

Seeds: Average amount; medium size.

*Plant*

Foliage:

*Leaves.*—Compound of 5 leaflets; abundant; large size; glossy.

*Leaflets.*—Shape — ovate. Apex. — acute. Base—round. Margin—serrate.

*Color.*—*Mature*: upper surface—near Spinach Green, Plate 0960, page 187; under surface—near Spinach Green, Plate 0960/2, page 187; Young: upper surface—near Lettuce Green, Plate 861, page 176, slightly overlaid with Pansy Purple, Plate 928/3, page 177; under surface—Lettuce Green, Plate 861/1, page 176, slightly overlaid with Pansy Purple, Plate 928/3, page 177.

*Rachis (the supporting stem of the compound leaf).*—medium heavy. Upper side—grooved.

Under side—medium smooth surface, with small thorns and prickles.

*Stipules.*—Long length; points turning out at an almost 45° angle.

Growth:

*Habit.*—Bush; upright.

*Growth.*—Vigorous.

*Canes.*—Large; strong.

*Main stems.*—Color—Spinach Green, Plate 0960/1, page 187, overlaid with streaks of near Garnet Brown, Plate 00918/3 page 192. *Thorns*—average amount, medium to long length; some pointing straight, some hooked downward; very sharp points; color—greyish brown (no color in chart listed). *Prickles*—several.

*Branch.*—Color—Spinach Green, Plate 0960/1, page 187. *Thorns*—average amount; medium length; hooked downward; very sharp points; Color—near Scheeles Green, Plate 860/3, page 175, with reddish brown points. *Prickles.*—few. *Hairs*—none.

*New Shoots.*—Color—Scheeles Green, Plate 860, page 175. *Thorns* — several; medium length; hooked downward; color—Lettuce Green, Plate 861/1, page 176. *Prickles*—few. *Hairs*—none.

I claim:

1. A new and distinct variety of rose plant of the grandiflora class, substantially as herein shown and described, characterized particularly as to novelty by the unique combination of good growing and flower producing habits, profuse glossy green foilage, relatively large flowers which are borne on strong, medium length stems, good flower form, good moderate fragrance, better than average disease resistance, attractive general color tonality of the flowers corresponding Cardinal in the newly open flowers, and to near Tyrian Purple, in the three-days open flowers, and good keeping qualities of flowers as cut flowers.

No references cited.

ROBERT E. BAGWELL, Primary Examiner